US008945869B2

(12) United States Patent
Cho et al.

(10) Patent No.: US 8,945,869 B2
(45) Date of Patent: *Feb. 3, 2015

(54) FACTOR VIII GLYCOFORMS

(75) Inventors: Myung-Sam Cho, Pinole, CA (US); Sham-Yuen Chan, El Sobrante, CA (US)

(73) Assignee: Bayer Healthcare LLC, Whippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/482,326

(22) Filed: May 29, 2012

(65) Prior Publication Data

US 2013/0143818 A1    Jun. 6, 2013

Related U.S. Application Data

(60) Continuation of application No. 12/941,685, filed on Nov. 8, 2010, now Pat. No. 8,207,117, which is a division of application No. 11/789,580, filed on Apr. 25, 2007, now abandoned, which is a continuation of application No. 10/225,900, filed on Aug. 22, 2002, now Pat. No. 7,459,525, which is a continuation-in-part of application No. 10/006,091, filed on Dec. 6, 2001, now abandoned, which is a continuation of application No. 09/209,916, filed on Dec. 10, 1998, now Pat. No. 6,358,703.

(51) Int. Cl.
*C12P 21/06* (2006.01)
*C07K 14/755* (2006.01)

(52) U.S. Cl.
CPC ......... *C07K 14/755* (2013.01); *C12N 2799/028* (2013.01)
USPC ............ 435/69.1; 435/6; 435/7.1; 435/320.1

(58) Field of Classification Search
None
See application file for complete search history.

(56) References Cited

U.S. PATENT DOCUMENTS

| | | | |
|---|---|---|---|
| 4,377,513 A | 3/1983 | Sugimoto et al. | |
| 4,703,008 A | 10/1987 | Lin | |
| 4,757,006 A | 7/1988 | Toole, Jr. et al. | |
| 4,766,075 A | 8/1988 | Goeddel et al. | |
| 4,816,397 A | 3/1989 | Boss et al. | |
| 4,868,112 A | 9/1989 | Toole, Jr. | |
| 4,965,199 A | 10/1990 | Capon et al. | |
| 4,970,300 A | 11/1990 | Fulton et al. | |
| 5,171,844 A | 12/1992 | van Ooyen et al. | |
| 5,198,349 A | 3/1993 | Kaufman | |
| 5,612,213 A | 3/1997 | Chan | |
| 5,661,008 A | 8/1997 | Almstedt et al. | |
| 5,804,420 A | 9/1998 | Chan et al. | |
| 5,952,198 A | 9/1999 | Chan | |
| 6,136,599 A | 10/2000 | Cho | |
| 6,180,108 B1 | 1/2001 | Cho et al. | |
| 6,358,703 B1 | 3/2002 | Cho et al. | |
| 6,528,286 B1 | 3/2003 | Ryll | |
| 7,459,525 B2 | 12/2008 | Cho et al. | |

FOREIGN PATENT DOCUMENTS

| | | |
|---|---|---|
| EP | 0 254 076 | 1/1988 |
| EP | 0260148 A2 | 3/1988 |
| GB | 2 085 887 | 5/1982 |
| WO | WO-91/09122 | 6/1991 |
| WO | WO-97/12915 | 4/1997 |
| WO | WO-9749725 A1 | 12/1997 |
| WO | WO-0034505 A1 | 6/2000 |

OTHER PUBLICATIONS

ReFacto® BDD Factor VIII SQ Product Information Insert, Revised May 2002.
Vehar et al., Structure of Human Factor VIII. *Nature* 312:337-342 (Nov. 1984).
Wood et al., Expression of Active Human Factor VIII from Recombinant DNA Clones. *Nature* 312:330-337 (Nov. 1984).
Toole et al., Molecular Cloning of a DNA Encoding Human Antihaemophilic Factor. Nature 312:342-347 (Nov. 1984).
Gitschier et al., Characterization of the Human Factor VIII Gene. *Nature* 312:326-330 (Nov. 1984).
Lenting et al., The Life Cycle of Coagulation Factor VIII in View of its Structure and Function. *Blood* 92(11):3983-3996 (1998).
Thompson AR, Structure and Function of the Factor VIII Gene and Protein. *Seminars in Thombosis and Hemostasis* 29(1):11-22 (2003).
Tajima et al., Characterization of "B Domain" Lacked Recombinant Factor VIII. *Proc. 6th Int. Symp. H. T.* 1990, 51-63.
Lollar, P. Structure and function of Factor VIII. In *Inhibitors to Coagulation Factors*, L.M. Aledort et al., eds. New York: Plenum Press, 1995, pp. 3-17.
Lind, P. et al. Novel forms of B-domain-deleted recombinant factor VIII molecules: Construction and biochemical characterization. Eur. J. Biochem. 232, 1995, 19-27.
Cho et al. Establishment of a Human Somatic Hybrid Cell Line for Recombinant Protein Production. *Journal of Biomedical Science* 9:631-638 (2002).
Wells, *Biochemistry*, vol. 29, pp. 8509-8517, 1990.
Seffernick et al., *J. Bacteriology*, vol. 183, pp. 2405-2410, 2001.
Sandberg, H. et al. *Seminars in Hematology*, vol. 38, No. 2, Suppl. 4, pp. 4-12 (2001).
Pu et al., Rapid Establishment of High-Producing Cell Lines Using Dicistronic Vectors and Glutamine Synthetase as the Selection Marker. *Mol. Biotechnol.* 10: 17-25 (1998).
Kane, S.E. Selection of Transfected Cells and Coamplification of Transfected Genes. *Methods Mol. Biol.* 62: 359-367 (1997).
Bebbington et al., High-level Expression of a Recombinant Antibody from Myeloma Cells using a Glutamine Synthetase Gene as an Amplifiable Selection Marker. *Bio/Technol.* 10: 169-175 (Feb. 1992).

(Continued)

*Primary Examiner* — Hope Robinson
(74) *Attorney, Agent, or Firm* — Buchanan Ingersoll & Rooney PC

(57) ABSTRACT

The invention concerns glycosylated proteins having human factor VIII activity. In a preferred embodiment, the protein is glycosylated with oligosaccharides that include an alpha-(2, 6)-linked sialic acid and a bisecting GlcNAc linked to a core beta-mannose.

38 Claims, 7 Drawing Sheets

(56) References Cited

OTHER PUBLICATIONS

Kemball-Cook, et al., "The Factor VIII Structure and Mutation Resource Site: HAMSTeRS Version 4", Nucleic Acid Research, 1998, vol. 26, No. 1, pp. 216-219.
Stillman et al., Replication and Supercoiling of Simian Virus 40 DNA in Cell Extracts from Human Cells, Molecular and Cellular Biology, 1985, vol. 5, No. 8, pp. 2051-2060.
Peshaw et al., "Cultivation of Mammalian Cells as Aggregates in Bioreactors: Effect of Calcium Concentration on Spatial Distribution of Viability", Biotechnology and Bioengineering, 1993, vol. 41, pp. 179-187.
Ragheb et al., "The Amphotropic and Ecotropic Murine Leukemia Virus Envelope TM Subunits are Equivalent Mediators of Direct Membrane Fusion: Implications for the Role of the Ecotropic Envelope and Receptor in Syncytium Formation and Viral Entry", Journal of Virology, 1995, vol. 69, No. 11, pp. 7205-7215.
Walls et al., Amplification of multicistronic plasmids in the human 293 cell line and secretion of correctly processed recombinant human protein C, Gene, 1989, vol. 81, pp. 139-149.
Guo et al., "Protein Tolerance to Random Amino Acid Change", PNAS, 2004, vol. 101, No. 25, pp. 9205-9210.
Hironaka et al., (J. Biological Chemistry, 1992, pp. 8012-8020).
Medzihradszky et al., (Anal. Chem. 1997, vol. 69, pp. 3986-3994).
Matsui et al., (J. Biological Chemistry, 1992, vol. 267, pp. 8723-8731).
Kumar et al. (Biotechnol. Appl. Biochem., vol. 24, 1996, pp. 207-216).

```
   1  ATRRYYLGAV  ELSWDYMQSD  LGELPVDARF  PPRVPKSFPF  NTSVVYKKTL
  51  FVEFTVHLFN  IAKPRPPWMG  LLGPTIQAEV  YDTVVITLKN  MASHPVSLHA
 101  VGVSYWKASE  GAEYDDQTSQ  REKEDDKVFP  GGSHTYVWQV  LKENGPMASD
 151  PLCLTYSYLS  HVDLVKDLNS  GLIGALLVCR  EGSLAKEKTQ  TLHKFILLFA
 201  VFDEGKSWHS  ETKNSLMQDR  DAASARAWPK  MHTVNGYVNR  SLPGLIGCHR
 251  KSVYWHVIGM  GTTPEVHSIF  LEGHTFLVRN  HRQASLEISP  ITFLTAQTLL
 301  MDLGQFLLFC  HISSHQHDGM  EAYVKVDSCP  EEPQLRMKNN  EEAEDYDDDL
 351  TDSEMDVVRF  DDDNSPSFIQ  IRSVAKKHPK  TWVHYIAAEE  EDWDYAPLVL
 401  APDDRSYKSQ  YLNNGPQRIG  RKYKKVRFMA  YTDETFKTRE  AIQHESGILG
 451  PLLYGEVGDT  LLIIFKNQAS  RPYNIYPHGI  TDVRPLYSRR  LPKGVKHLKD
 501  FPILPGEIFK  YKWTVTVEDG  PTKSDPRCLT  RYYSSFVNME  RDLASGLIGP
 551  LLICYKESVD  QRGNQIMSDK  RNVILFSVFD  ENRSWYLTEN  IQRFLPNPAG
 601  VQLEDPEFQA  SNIMHSINGY  VFDSLQLSVC  LHEVAYWYIL  SIGAQTDFLS
 651  VFFSGYTFKH  KMVYEDTLTL  FPFSGETVFM  SMENPGLWIL  GCHNSDFRNR
 701  GMTALLKVSS  CDKNTGDYYE  DSYEDISAYL  LSKNNAIEPR  SFSQNPPVLK
 751  RHQREITRTT  LQSDQEEIDY  DDTISVEMKK  EDFDIYDEDE  NQSPRSFQKK
 801  TRHYFIAAVE  RLWDYGMSSS  PHVLRNRAQS  GSVPQFKKVV  FQEFTDGSFT
 851  QPLYRGELNE  HLGLLGPYIR  AEVEDNIMVT  FRNQASRPYS  FYSSLISYEE
 901  DQRQGAEPRK  NFVKPNETKT  YFWKVQHHMA  PTKDEFDCKA  WAYFSDVDLE
 951  KDVHSGLIGP  LLVCHTNTLN  PAHGRQVTVQ  EFALFFTIFD  ETKSWYFTEN
1001  MERNCRAPCN  IQMEDPTFKE  NYRFHAINGY  IMDTLPGLVM  AQDQRIRWYL
1051  LSMGSNENIH  SIHFSGHVFT  VRKKEEYKMA  LYNLYPGVFE  TVEMLPSKAG
1101  IWRVECLIGE  HLHAGMSTLF  LVYSNKCQTP  LGMASGHIRD  FQITASGQYG
1151  QWAPKLARLH  YSGSINAWST  KEPFSWIKVD  LLAPMIIHGI  KTQGARQKFS
1201  SLYISQFIIM  YSLDGKKWQT  YRGNSTGTLM  VFFGNVDSSG  IKHNIFNPPI
1251  IARYIRLHPT  HYSIRSTLRM  ELMGCDLNSC  SMPLGMESKA  ISDAQITASS
1301  YFTNMFATWS  PSKARLHLQG  RSNAWRPQVN  NPKEWLQVDF  QKTMKVTGVT
1351  TQGVKSLLTS  MYVKEFLISS  SQDGHQWTLF  FQNGKVKVFQ  GNQDSFTPVV
1401  NSLDPPLLTR  YLRIHPQSWV  HQIALRMEVL  GCEAQDLY
```

Fig. 1

```
GGCAATGGAG  CGTGAAGAAG  GGCCCCAGGG  CTGACCCCGG  CAAACGTGAC   (50)
CCGGGGCTCC  GGGGTGACCC  AGGCAAGCGT  GGCCAAGGGG  CCCGTGGGTG  (100)
ACACAGGCAA  CCCTGACAAA  GGCCCCCCAG  GAAAGACCCC  CGGGGGGCAT  (150)
CGGGGGGGTG  TTGGCGGGTC  ATGGGGGGGG  CGGGTCATGC  CGCGCATTCC  (200)
TGGAAAAAGT  GGAGGGGGCG  TGGCCTTCCC  CCCGCGGCCC  CCTAGCCCCC  (250)
CCGCAGAGAG  CGGCGCAACG  GCGGGCGAGC  GGCGGGGGGT  CGGGGTCCGC  (300)
GGGCTCCGGG  GGCTGCGGGC  GGTGGATGGC  GGCTGGCGTT  CCGGGGATCG  (350)
GGGGGGGGTC  GGGGGGCGCT  GCGCGGGCGC  AGCCATGCGT  GACCGTGATG  (400)
AG                                                          (402)
```

Fig. 2

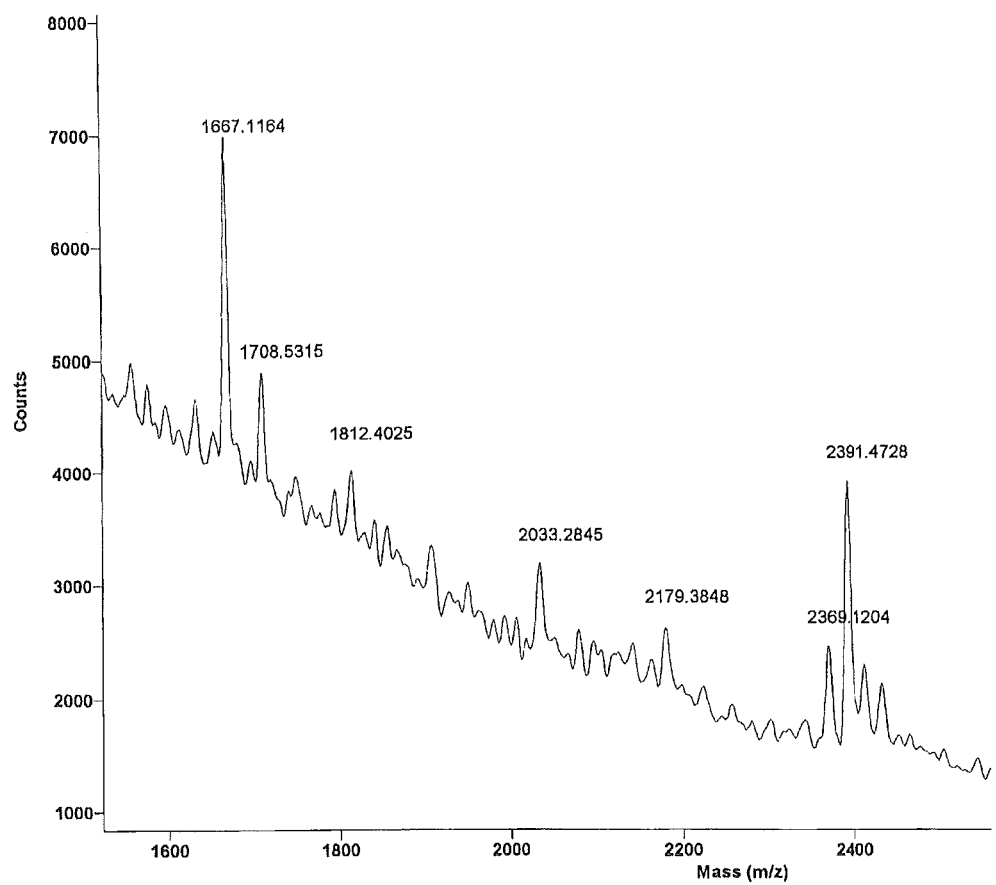
Fig. 7. MALDI mass spectrometric analysis of BDD FVIII-SQ.

SEQUENCE LISTING

```
<160> NUMBER OF SEQ ID NOS: 2

<210> SEQ ID NO 1
<211> LENGTH: 1438
<212> TYPE: PRT
<213> ORGANISM: Artificial Sequence
<220> FEATURE:
<223> OTHER INFORMATION: Description of Artificial Sequence:  Derived
      from human factor VIII sequence

<400> SEQUENCE: 1

Ala Thr Arg Arg Tyr Tyr Leu Gly Ala Val Glu Leu Ser Trp Asp Tyr
 1               5                  10                  15

Met Gln Ser Asp Leu Gly Glu Leu Pro Val Asp Ala Arg Phe Pro Pro
             20                  25                  30

Arg Val Pro Lys Ser Phe Pro Phe Asn Thr Ser Val Val Tyr Lys Lys
         35                  40                  45

Thr Leu Phe Val Glu Phe Thr Val His Leu Phe Asn Ile Ala Lys Pro
     50                  55                  60

Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220
```

```
Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
            245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Leu Thr Asp
                340                 345                 350

Ser Glu Met Asp Val Val Arg Phe Asp Asp Asn Ser Pro Ser Phe
            355                 360                 365

Ile Gln Ile Arg Ser Val Ala Lys Lys His Pro Lys Thr Trp Val His
370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
        450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
```

-continued

```
                645                 650                 655
Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
            690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Val Leu Lys Arg His
                740                 745                 750

Gln Arg Glu Ile Thr Arg Thr Leu Gln Ser Asp Gln Glu Ile
                755                 760                 765

Asp Tyr Asp Asp Thr Ile Ser Val Glu Met Lys Lys Glu Asp Phe Asp
770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Pro His Val Leu Arg Asn Arg Ala Gln Ser Gly Ser
                820                 825                 830

Val Pro Gln Phe Lys Lys Val Val Phe Gln Glu Phe Thr Asp Gly Ser
                835                 840                 845

Phe Thr Gln Pro Leu Tyr Arg Gly Glu Leu Asn Glu His Leu Gly Leu
850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
                900                 905                 910

Val Lys Pro Asn Glu Thr Lys Thr Tyr Phe Trp Lys Val Gln His His
                915                 920                 925

Met Ala Pro Thr Lys Asp Glu Phe Asp Cys Lys Ala Trp Ala Tyr Phe
                930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975

Val Thr Val Gln Glu Phe Ala Leu Phe Phe Thr Ile Phe Asp Glu Thr
                980                 985                 990

Lys Ser Trp Tyr Phe Thr Glu Asn Met Glu Arg Asn Cys Arg Ala Pro
                995                 1000                1005

Cys Asn Ile Gln Met Glu Asp Pro Thr Phe Lys Glu Asn Tyr Arg Phe
    1010                1015                1020

His Ala Ile Asn Gly Tyr Ile Met Asp Thr Leu Pro Gly Leu Val Met
1025                1030                1035                1040

Ala Gln Asp Gln Arg Ile Arg Trp Tyr Leu Leu Ser Met Gly Ser Asn
                1045                1050                1055

Glu Asn Ile His Ser Ile His Phe Ser Gly His Val Phe Thr Val Arg
                1060                1065                1070
```

-continued

Lys Lys Glu Glu Tyr Lys Met Ala Leu Tyr Asn Leu Tyr Pro Gly Val
1075                1080                1085

Phe Glu Thr Val Glu Met Leu Pro Ser Lys Ala Gly Ile Trp Arg Val
1090                1095                1100

Glu Cys Leu Ile Gly Glu His Leu His Ala Gly Met Ser Thr Leu Phe
1105                1110                1115                1120

Leu Val Tyr Ser Asn Lys Cys Gln Thr Pro Leu Gly Met Ala Ser Gly
1125                1130                1135

His Ile Arg Asp Phe Gln Ile Thr Ala Ser Gly Gln Tyr Gly Gln Trp
1140                1145                1150

Ala Pro Lys Leu Ala Arg Leu His Tyr Ser Gly Ser Ile Asn Ala Trp
1155                1160                1165

Ser Thr Lys Glu Pro Phe Ser Trp Ile Lys Val Asp Leu Leu Ala Pro
1170                1175                1180

Met Ile Ile His Gly Ile Lys Thr Gln Gly Ala Arg Gln Lys Phe Ser
1185                1190                1195                1200

Ser Leu Tyr Ile Ser Gln Phe Ile Ile Met Tyr Ser Leu Asp Gly Lys
1205                1210                1215

Lys Trp Gln Thr Tyr Arg Gly Asn Ser Thr Gly Thr Leu Met Val Phe
1220                1225                1230

Phe Gly Asn Val Asp Ser Ser Gly Ile Lys His Asn Ile Phe Asn Pro
1235                1240                1245

Pro Ile Ile Ala Arg Tyr Ile Arg Leu His Pro Thr His Tyr Ser Ile
1250                1255                1260

Arg Ser Thr Leu Arg Met Glu Leu Met Gly Cys Asp Leu Asn Ser Cys
1265                1270                1275                1280

Ser Met Pro Leu Gly Met Glu Ser Lys Ala Ile Ser Asp Ala Gln Ile
1285                1290                1295

Thr Ala Ser Ser Tyr Phe Thr Asn Met Phe Ala Thr Trp Ser Pro Ser
1300                1305                1310

Lys Ala Arg Leu His Leu Gln Gly Arg Ser Asn Ala Trp Arg Pro Gln
1315                1320                1325

Val Asn Asn Pro Lys Glu Trp Leu Gln Val Asp Phe Gln Lys Thr Met
1330                1335                1340

Lys Val Thr Gly Val Thr Thr Gln Gly Val Lys Ser Leu Leu Thr Ser
1345                1350                1355                1360

Met Tyr Val Lys Glu Phe Leu Ile Ser Ser Ser Gln Asp Gly His Gln
1365                1370                1375

Trp Thr Leu Phe Phe Gln Asn Gly Lys Val Lys Val Phe Gln Gly Asn
1380                1385                1390

Gln Asp Ser Phe Thr Pro Val Val Asn Ser Leu Asp Pro Pro Leu Leu
1395                1400                1405

Thr Arg Tyr Leu Arg Ile His Pro Gln Ser Trp Val His Gln Ile Ala
1410                1415                1420

Leu Arg Met Glu Val Leu Gly Cys Glu Ala Gln Asp Leu Tyr
1425                1430                1435

<210> SEQ ID NO 2
<211> LENGTH: 402
<212> TYPE: DNA
<213> ORGANISM: Artificial Sequence
<220> FEATURE:
<223> OTHER INFORMATION: Description of Artificial Sequence:Derived from
      Epstein-Barr virus sequence

```
<400> SEQUENCE: 2
ggcaatggag cgtgacgaag ggccccaggg ctgaccccgg caaacgtgac ccggggctcc      60
ggggtgaccc aggcaagcgt ggccaagggg cccgtgggtg acacaggcaa ccctgacaaa     120
ggccccccag gaaagacccc cggggggcat cggggggggtg ttggcgggtc atggggggggg     180 cgggtcatgc cgcgcattcc tggaaaaagt ggaggggggcg tggccttccc cccgcggccc     240
cctagccccc ccgcagagag cggcgcaacg gcgggcgagc ggcggggggt cggggtccgc     300
gggctccggg ggctgcgggc ggtggatggc ggctggcgtt ccggggatcg gggggggggtc     360 ggggggcgct gcgcgggcgc agccatgcgt gaccgtgatg ag                        402
```

FACTOR VIII GLYCOFORMS

This application is a continuation of U.S. application Ser. No. 12/941,685 filed Nov. 8, 2010 which is hereby incorporated by reference herein in its entirety, which is a divisional of U.S. application Ser. No. 11/789,580, filed on Apr. 25, 2007, now abandoned, which is hereby incorporated by reference herein in its entirety, which is a continuation of U.S. application Ser. No. 10/225,900, filed Aug. 22, 2002, now U.S. Pat. No. 7,459,525, which is hereby incorporated by reference herein in its entirety, which is a continuation-in-part of U.S. application Ser. No. 10/006,091, filed Dec. 6, 2001, now abandoned, which is a continuation of Ser. No. 09/209,916 filed Dec. 10, 1998, now U.S. Pat. No. 6,358,703, which is hereby incorporated by reference herein in its entirety.

BACKGROUND OF THE INVENTION

1. Field

The present invention relates to factor VIII glycoforms. In particular, this invention relates to a recombinantly produced factor VIII that has a glycosylation pattern resembling the glycosylation pattern of naturally occurring human Factor VIII.

2. Background

Human factor VIII is a trace plasma glycoprotein involved as a cofactor in the activation of factor X and factor IXa. Inherited deficiency of factor VIII results in the X-linked bleeding disorder hemophilia A, which can be treated successfully with purified factor VIII. The replacement therapy of hemophilia A has evolved from the use of plasma-derived factor VIII to the use of recombinant factor VIII obtained by cloning and expressing the factor VIII cDNA in mammalian cells. (Wood et al., 1984, Nature 312: 330).

Human factor VIII has a polypeptide molecular weight of 265,000. Factor VIII has three types of domains. It has a domain organization of A1-A2-B-A3-C1-C2 and is synthesized as a single chain polypeptide of 2351 amino acids, from which a 19-amino acid signal peptide is cleaved upon translocation into the lumen of the endoplasmic reticulum. The B domain contains up to 50% of the mass of the factor VIII and has no known function. Due to proteolysis within the B domain and between the A2 and B domains, plasma-derived and recombinant factor VIII are isolated as a heterogeneous population of heterodimers with little or no single chain factor VIII present. It is likely that factor VIII circulates in predominantly heterodimeric form. (Lollar, Peter, 1995, Inhibitors to Coagulation Factors, edited by Louis Aledort et al., Plenum Press, pp. 3-17).

Factor VIII is also described as consisting of three major regions: an N-terminal 90-kd heavy chain, a C-terminal 80-kd light chain, and the central B domain.

Factor VIII is heavily glycosylated. Glycosylation involves the modification of the polypeptide backbone with one or more oligosaccharide groups. Glycosylation can dramatically affect the physical properties of proteins and can also be important in protein stability, secretion, and subcellular localization. Proper glycosylation can be essential for a protein's biological activity. For example, the circulation half-life of recombinant erythropoietin, a hormone involved in the regulation of the level of red blood cells, was greatly increased when its glycosylation pattern was changed. For years Amgen discarded 80% of the recombinant erythropoietin it generated because of inadequate glycosylation, which resulted in unacceptably rapid clearing from the blood. When two extra sugars were added to those normally found on erythropoietin, a new drug, sold as ARANSEP®, was developed that stays in the blood roach longer than the original drug and thus requires less frequent dosing. (Maeder, Thomas, Sci. Amer., July 2002, pp. 40-47).

The oligosaccharide groups that create mammalian glycosylation patterns are derived from roughly ten simple sugars that can join with each other at many different points to form intricate branching patterns. Not only can a sugar add to another sugar at many different locations in the first sugar's structure, but the addition can also be in different orientations such as when the newly added sugar points above or below the plane of the ring of the first sugar. Because of these two factors, even the simplest sugars in the human body can combine in so many different ways that more than 15 million four-component oligosaccharides are theoretically possible. (Id.).

Glycosylation occurs at specific locations on the polypeptide backbone. It occurs typically when O-linked oligosaccharides are attached to threonine or serine residues and when N-linked oligosaccharides are attached to asparagine residues when they are part of the sequence Asn-X-Ser/Thr, where X can be any amino acid except proline. Although different oligosaccharides are present in glycosylation, one sugar, N-acetylneuraminic acid (commonly known as sialic acid), is commonly found on both N-linked and O-linked oligosaccharides. Sialic acid is usually the terminal sugar residue on N-linked and O-linked oligosaccharides.

Human factor VIII has 25 potential N-linked glycosylation sites, 19 of which are in the B domain. Of the glycosylation sites in the B domain, at least 75% are occupied. The A1 subunit has two potential N-linked glycosylation sites, at least one of which is occupied. The A2 subunit has a single unoccupied site. The light chain (subunits A3, C1 and C2) has two potential N-linked glycosylation sites, at least one of which is occupied. (Lollar, supra, at 1-5).

Due to the fact that factor VIII is heavily glycosylated, high-level expression (>0.2 pg/c/d) of recombinant factor VIII has been difficult to achieve (Lind et al., 1995, Eur J Biochem. 232: 19-27; Kaufman et al., 1989, Mol Cell Biol. 9: 1233-1242). Expression of factor VIII in mammalian cells is typically 2-3 orders of magnitude lower than that observed with other genes using similar vectors and approaches. The productivity of production cell lines for factor VIII has been in the range of 0.5-1 µU/c/d (0.1-0.2 pg/c/d).

It has been demonstrated that the B-domain of factor VIII is dispensable for procoagulant activity. Because the majority of the glycosylation sites are in the B domain, the overall size of the full-length factor VIII molecule is greatly decreased by deleting this domain. Using truncated variants of factor VIII, improved expression of factor VIII in mammalian cells has been reported by various groups (Lind et al., 1995, Eur J Biochem. 232: 19-27; Tajima et al., 1990, Proc $6^{th}$ Int Symp H.T. p. 51-63; U.S. Pat. No. 5,661,008 to Almstedt, 1997). However, the expression level of the factor VIII variants remained below 1 pg/c/d from a stable cell clone.

Variants of B-domain deleted recombinant Factor VIII have been made. For example, one variant, referred to herein as BDD FVIII SQ (SEQ ID NO: 1), has been genetically engineered to replace the 908 amino acids of the B domain with a short 14 amino acid linker that is derived from the N- and C-terminal ends of the B domain. BDD FVIII SQ is sold by Wyeth/Genetics Institute under the trade name REFACTO®. It is produced in Chinese hamster ovary (CHO) cells and secreted as a heterodimer. (Sandberg, H. et al., 2001, Seminars in Hematology, Vol. 38, No. 2, Suppl., 4, pp. 4-12).

BDD FVIII SQ contains six consensus N-linked glycosylation sites. Three sites are in the heavy chain at $Asn^{41}$, $Asn^{239}$ and $Asn^{582}$ while three sites are in the light chain at $Asn^{1685}$, Asn$^{1810}$ and Asn$^{2118}$. In BDD FVIII SQ produced in CHO cells, four of the six N-linked consensus sites are glycosylated and no N-linked carbohydrate was detected at the remaining consensus sites. Glycosylation was noted at Asn$^{41}$, Asn$^{239}$, Asn$^{1810}$ and Asn$^{2118}$. Most of the glycans attached to Asn$^{239}$ and Asn$^{2118}$ are high-mannose structures, while the majority of the glycans at Asn$^{41}$ and Asn$^{1810}$ are of the complex type and were predominantly sialylated, core fucosylated, and bi- and tri-antennal glycans with poly-N-acetyllactosamine repeat units. (Id. at 8).

It is an object of the present invention to provide a recombinantly produced molecule having factor VIII activity for use as a human pharmaceutical that can be produced in high yield. It is believed that the biological efficacy of such a molecule would be enhanced by having a glycosylation pattern, including specific oligosaccharide structures, that resembles or is identical to the glycosylation pattern in naturally produced human factor VIII. In particular, it is believed that the in vivo half-life in humans of a protein having factor VIII activity would be increased if the protein had a human glycosylation pattern. Also, it is believed that such a protein may have a higher specific activity in vivo. Therefore, it is an object of the present invention to provide a molecule having factor VIII activity that also has one or more oligosaccharides attached at N-linked glycosylation sites that are identical to or closely resemble the oligosaccharides found at N-linked glycosylation sites in naturally produced human factor VIII.

SUMMARY OF THE INVENTION

We have now discovered an isolated glycosylated protein having factor VIII procoagulant activity and a human glycosylation pattern that can be produced in high yield. More particularly, the glycosylation pattern includes an N-linked oligosaccharide that contains alpha-(2,6)-linked sialic acid and a bisecting N-acetylglucosamine (GlcNAc) linked to a core beta-mannose. Because such a glycosylation pattern is present in naturally occurring human factor VIII, it is believed that the pharmaceutical properties of the inventive protein are superior to other isolated proteins having factor VIII activity but not an N-linked oligosaccharide that contains alpha-(2, 6)-linked sialic acid and/or a bisecting N-acetylglucosamine (GlcNAc) linked to a core beta-mannose.

BRIEF DESCRIPTION OF THE FIGURES

FIG. 1. Amino Acid Sequence of BDD FVIII SQ (SEQ ID NO:1).

FIG. 2. Sequence of terminal repeat (TR) sequence isolated from Epstein-Barr virus (SEQ ID NO:2).

FIG. 4(*b*). Comparison of productivities of several clones in various media. Three data points are presented from a two month stability test of each clone.

FIG. 7. MALDI mass spectrometric analysis of BDD FVIII SQ produced in HKB11 cells.

DETAILED DESCRIPTION OF THE INVENTION

Figure 3:
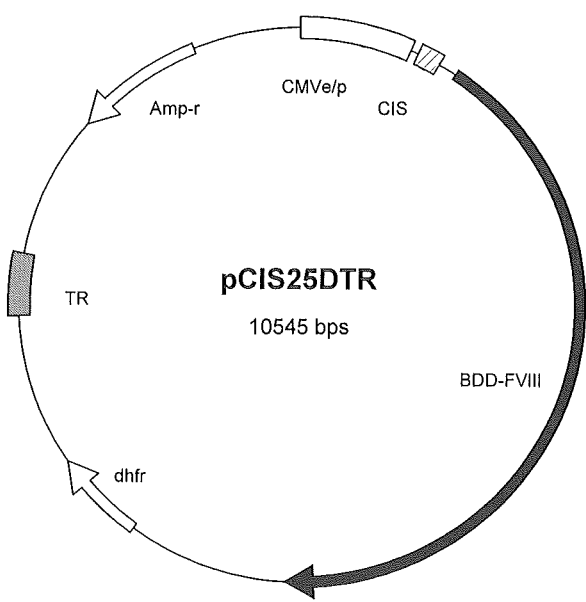
FIG. 3. Plasmid map of pCIS25DTR.

According to the present invention, isolated glycosylated proteins having factor VIII activity are provided. In a pre ferred embodiment, the protein is glycosylated with oligosaccharides that include an alpha-(2,6)-linked sialic acid and/or a bisecting GlcNAc linked to a core beta-mannose.

Preferably, the invention is directed to a glycosylated protein comprising the amino acid sequence of SEQ ID NO:1 and a human glycosylation pattern. More preferably, the invention is directed to a glycosylated protein comprising the amino acid sequence of SEQ ID NO:1 and oligosaccharide comprising alpha-(2,6)-linked sialic acid and/or a bisecting GlcNAc linked to a core beta-mannose. Preferably, this glycosylated protein is isolated.

In another embodiment, the invention is directed to a glycosylated protein having a 90-kd heavy chain and an 80-kd light chain linked by a linker polypeptide of about 14 amino acids, wherein the protein has factor VIII procoagulant activity in humans and a human glycosylation pattern. Preferably, the invention is directed to a glycosylated protein having a 90-kd heavy chain and an 80-kd light chain linked by a linker polypeptide of about 14 amino acids, wherein the protein has factor VIII procoagulant activity in humans and N-linked oligosaccharides comprising alpha-(2,6)-linked sialic acid and/or a bisecting GlcNAc linked to a core beta-mannose.

In another embodiment, the invention is directed to a protein having Factor VIII procoagulent activity, wherein the amino acid sequence of the protein and the amino acid sequence of SEQ ID NO:1 have at least 62% identity and the protein has an N-linked oligosaccharide comprising alpha-(2, 6)-linked sialic acid and/or a bisecting GlcNAc linked to a core beta-mannose. More preferably, the percent identity is at least 72%, still more preferably at least 82%, yet more preferably at least 92%, and still yet more preferably at least 95%.

Percent identity is determined from an optimal global alignment between the two sequences being compared. An optimal global alignment is achieved using, for example, the Needleman-Wunsch algorithm disclosed at Needleman and Wunsch, 1970, J. Mol. Biol. 48:443-453, which is hereby incorporated herein in its entirety. Preferably, percent identity is determined by using the Needle implementation of the Needleman-Wunsch algorithm, which is available at the website of the European Bioinformatics Institute, EMBL-EBI, www.ebi.ac.uk. "Identity" means that an amino acid at a particular position in a first polypeptide is identical to a corresponding amino acid in a second polypeptide that is in an optimal global alignment with the first polypeptide. By the statement "sequence A is n % identical to sequence B" is meant that n % of the positions of an optimal global alignment between sequences A and B consists of identical residues. Optimal global alignments in this disclosure used the following parameters in the Needleman-Wunsch alignment algorithm for polypeptides: Substitution matrix: blosum62. Gap scoring function: Gap penalty 10.0, Extend penalty 0.5.

The invention is also directed to pharmaceutical compositions comprising a therapeutically effective amount of one or more of the glycosylated proteins of the invention in admixture with a pharmaceutically acceptable adjuvant. Glycosylated proteins having Factor VIII activity are preferably administered parenterally. Preferred formulations for parenteral administration include buffered saline and albumin. Also preferred are the formulations disclosed in U.S. Pat. No. 5,763,401, issued Jun. 9, 1998 (Rajiv Nayar), which is hereby incorporated by reference herein in its entirety. Another preferred formulation includes sodium chloride, sucrose, L-histidine, calcium chloride and polysorbate 80.

Another preferred formulation includes sucrose, glycine, histidine, calcium chloride, sodium chloride, polysorbate 80, imidazole, tri-n-butyl phosphate and copper. Preferred formulations do not include any toxic agents, such as toxic solubilizing agents like sodium dodecyl sulfate (SDS).

The required dosages are within the skill of those in the art to determine. For example, minor hemorrhaging in a patient with severe hemophilia A may be treated with 10-20 international units (IU) per kg body weight, which can be repeated if evidence of further bleeding. Moderate to major hemorrhaging in such a patient may be treated with 15-30 IU per kg body weight, which can be repeated at 12-24 hours if needed. Major to life-threatening hemorrhaging in such a patient may be treated with an initial dose of 40-50 IU/kg repeated at a dose of 20-25 IU/kg every 8 to 12 hours. For major surgical procedures to such a patient, the protein can be administered preoperatively at 50 IU/kg repeated as necessary after 6 to 12 hours. One IU, as defined by the World Health Organization standard for blood coagulation Factor VIII, human, is approximately equal to the level of Factor VIII activity found in 1 mL of fresh pooled human plasma.

The invention is also directed to methods of treating a factor VIII-associated disorder such as hemophilia by administering to a human in need thereof a therapeutically effective amount of the pharmaceutical compositions of the invention. The invention is also directed to methods of preparing one of the pharmaceutical compositions of the invention by mixing the protein having factor VIII procoagulent activity with a pharmaceutically acceptable adjuvant.

Preferably, the glycosylated protein is the product of recombinant cell production, and the glycosylation is the result of the normal post-translational cell functioning of the host cell. For example, the vector and cell line described in Example 1 infra can be used to produce the glycosylated protein of the invention.

Alternatively, glycosylation can be achieved through chemical modification of a protein having factor VIII activity. In yet a further alternative, the protein can be glycosylated by the addition of an enzyme that acts to add alpha-(2,6)-linked sialic acid to a host cell that expresses the protein having factor VIII activity but does not endogenously produce such an enzyme. For example, dihydrofolate reductase (dhfr) deficient CHO cells are commonly used host cells for recombinant glycoprotein production. Yet CHO cells do not endogenously express the enzyme beta-galactoside alpha-2,6 sialyltransferase, which is used to add sialic acid in the 2,6 linkage to galactose on the mannose alpha-1,3 branch. To add sialic acid at this linkage to a protein produced in CHO cells, the CHO cells can be transfected with a functional beta-galactosidase alpha-2,6 sialyltransferase gene to allow for incorporation of sialic acid in the 2,6 linkage to galactose as desired. (See Lee et al., J. Biol. Chem., 1989, 264:13848 for discussion of techniques for creating modified CHO cells).

Similarly, a bisecting GlcNAc can be added to a recombinantly produced protein having factor VIII activity by transfecting a host cell that does not endogenously produce this oligosaccharide linkage with the functional gene for the enzyme N-acetylglucosaminyltransferase, which has been reported to catalyze formation of a bisecting GlcNAc structure.

The proteins of the present invention can be produced at the industrial scale using the newly created cell host described in Example 1 at specific productivities in the range of 2-4 pg/cell/day (10-20 μU/c/d). Under serum-free conditions, one clone has sustained a daily productivity of 2-4 pg/c/d. Clones with this high level of productivity are able to produce 3-4 million units per day in a 15-liter perfusion fermenter. One unit of factor VIII activity is by definition the activity present in one milliliter of plasma. One pg of factor VIII is generally equivalent to about 5 μU of factor VIII activity.

As used herein, a protein having factor VIII procoagulant activity is a protein that causes the activation of factor X in an in vitro or in vivo model system. As non-limiting examples, this definition includes full-length recombinant human factor VIII and BDD FVIII SQ (SEQ ID NO: 1) whose sequence is described in FIG. 1.

As used herein, a human glycosylation pattern in a protein having factor VIII activity is a pattern of O- or N-linked oligosaccharides that are found in naturally occurring human factor VIII, when only the oligosaccharides in the domains or attached to the N- and O-linked glycosylation sites that are shared in common between the protein and naturally occurring factor VIII are compared. For example, in a recombinant B domain-deleted factor VIII, a human glycosylation pattern is found when the same N- or O-linked oligosaccharides found in naturally occurring human factor VIII (excepting those in the B domain) are found in the recombinant B domain-deleted factor VIII.

It is understood that the inventive glycosylated proteins may contain other oligosaccharides in addition to the two specified oligosaccharides discussed herein, namely, alpha-(2,6)-linked sialic acid and/or a bisecting GlcNAc linked to a core beta-mannose.

As used herein, an isolated protein is a protein substantially free of other proteins. For example, isolated proteins of the invention are at least 50%, more preferably at least 75% and still more preferably at least 90% by weight of the total protein matter present. An isolated protein having Factor VIII procoagulent activity preferably has an activity of greater than 5000 IU/mg protein, and more preferably has an activity of greater than 10,000 IU/mg protein.

In the case of amino acid sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Proteins referred to herein as "recombinant" are proteins or polypeptides produced by the expression of recombinant nucleic acids.

A high level of expression of a protein having factor VIII procoagulant activity means at least about 2 μU/c/d, or more preferably at least about 4 μU/c/d, or most preferably at least about 5 μU/c/d, of factor VIII activity if grown in plasma derived protein-free medium, or at least about 4 μU/c/d, or more preferably at least about 8 μU/c/d, or most preferably at least about 10 μU/c/d, of factor VIII activity if grown in medium supplemented with plasma derived protein. When the protein expressed is BDD-FVIII, cell lines having specific productivities up to about 15 μU/c/d, more preferably up to about 20 μU/c/d may be obtained by the method described herein.

As used herein to describe the origin of cell lines, "derived from" is intended to include, but not be limited to, normal mitotic cell division and processes such as transfections, cell fusions, or other genetic engineering techniques used to alter cells or produce cells with new properties.

EXAMPLES

Example 1

Preparation of BDD FVIII SQ 1.1 FVIII Assay

The activity of factor VIII derivatives obtained from recombinant gene expression in methotrexate (MTX)-resistant cell populations was measured by a chromogenic assay. Activity was quantitated using COATEST® factor VII:C/4 kit (Cromogenix, Molndal, Sweden) according to manufacturer's instructions. A U.S. standard anti-hemophilic factor (factor VIII) known as MEGA 1 (Office of Biologics Research and Review, Bethesda, Md.) was used as the standard of measurement in this assay (see Barrowcliffe, 1993, Thromb Haem 70: 876).

1.2 Construction of Expression Vectors for B-Domain Deleted FVIII

The sequence of the BDD FVIII SQ is shown in FIG. 1. The 90-kD and 80-kD chains were linked by a linker consisting of 14 amino acids. (See U.S. Pat. No. 5,952,198, issued Sep. 14, 1999 (Sham-Yuen Chan) for production method, which is hereby incorporated by reference herein in its entirety). The expression vector for BDD FVIII SQ was made using standard recombinant DNA techniques. The structure of the expression vector (pCIS25DTR) is shown in FIG. 3. The vector includes a transcriptional unit for BDD FVIII SQ and a selectable marker, dihydrofolate reductase (dhfr). In addition, a terminal repeat sequence from Epstein-Barr virus, which shows enhanced drug selection ratio, (FIG. 2) was inserted into the vector to increase the integration efficiency. The vector is essentially a construct of a vector (deposited ATCC 98879) that has been engineered to include a transcriptional unit corresponding to the sequence shown in FIG. 1. (See U.S. Pat. No. 6,180,108, issued Jan. 30, 2001 (Myung-Sam Cho and Sham-Yuen Chan) for discussion of the terminal repeat sequence, which is hereby incorporated herein in its entirety).

Similar vectors can be constructed and used by those having skill in the art to obtain cells expressing proteins having factor VIII procoagulant activity. For example, coding sequences coding for known variants of factor VIII which retain procoagulant activity can be substituted for the BDD FVIII SQ coding sequence. Also, instead of dhfr, other selectable markers can be used, such as glutamine synthetase (gs) or multidrug-resistance gene (mdr). The choice of a selection agent must be made accordingly, as is known in the art, i.e. for dhfr, the preferred selection agent is methotrexate, for gs the preferred selection agent is methionine sulfoximine, and for mdr the preferred selection agent is colchicine.

1.3 Derivation of Cell Lines Expressing BDD FVIII SQ: Transfection, Drug Selection and Gene Amplification Thirty micrograms of pCIS25DTR DNA was transferred into HKB11 (ATCC deposit no. CRL 12568), which is a hybrid of 293S cells and human Burkitt's lymphoma cells. (See U.S. Pat. No. 6,136,599, issued Oct. 24, 2000 (Myung-Sam Cho), incorporated herein by reference in its entirety). The DNA was transferred into the cells by electroporation set at 300 volts and 300 micro farads (BTX Electro cell Manipulator 600) using a 2 min cuvette (BTX part #620). In comparative experiments done to parallel work with the HKB11 cells, CHO (Chinese hamster ovary) and 293S (human embryonic kidney) cells were transfected using a cationic lipid reagent DMRIE-C (Life Technologies, Gaithersburg, Md.) according to a protocol provided by the Life Technologies. Amplification of transfected cells was done with increasing methotrexate (MTX) concentrations (100 nM, 200 nM, 400 nM, and 800 nM) at $1\times10^6$ cells per 96 well plate in a MTX-selection medium lacking hypoxanthine and thymidine (DME/F12 media without hypoxanthine and thymidine plus 5% dialyzed fetal bovine serum from Hyclone, Logan, Utah). MTX resistant cells were scored for growth, and secretion of the BDD-FVIII was screened using a COATEST® factor VIII kit about 2-3 weeks post-transfection. The cultivation of cells were done at 37° C. in a humidified 5% $CO_2$ incubator.

1.4 Limiting Dilution Cloning

Single cell clones (SCC) were derived by limiting dilution cloning (LDC) of high producing populations in 96 well plates under serum-free conditions. Cells were seeded at 1-10 cells per well in DME/F12 media supplemented with HUMULIN® recombinant insulin (Lilly, Indianapolis, Ind.) at 10 µg/ml, 10× essential amino acids (Life Technology, Gaithersburg, Md.), and PLASMANATE® human plasma protein fraction (Bayer, Clayton, N.C.). PLASMANATE® human plasma protein (HPP) fraction contains human albumin (88%) and various globulins (12%). The clones were screened for BDD-FVIII productivity using the COATEST® factor VIII kits. The highest producing clones were selected for stability evaluation in shake flasks. For HKB cells, the first round LDC was performed using selection medium supplemented with 5% dialyzed FBS. The second round LDC was done in serum-free but PLASMANATE® HPP fraction-containing medium using the first SCC adapted in serum-free medium supplemented with PLASMANATE® HPP fraction.

1.5 Derivation of HKB Clone 20B8

Figure 4A:
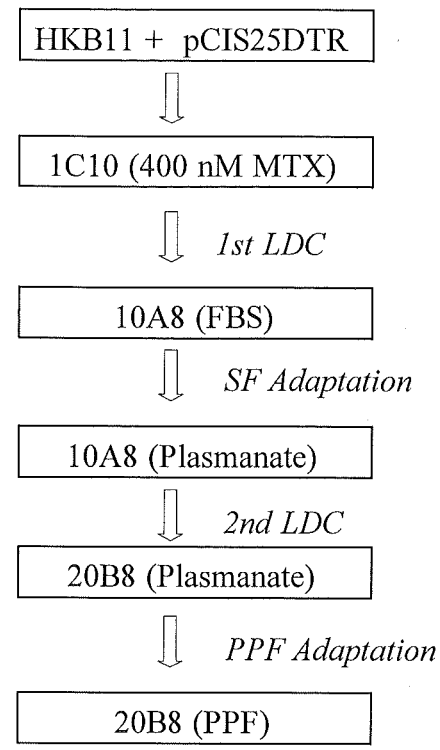
FIG. 4(*a*). Derivation of clone 20B8.
Figure 4B:
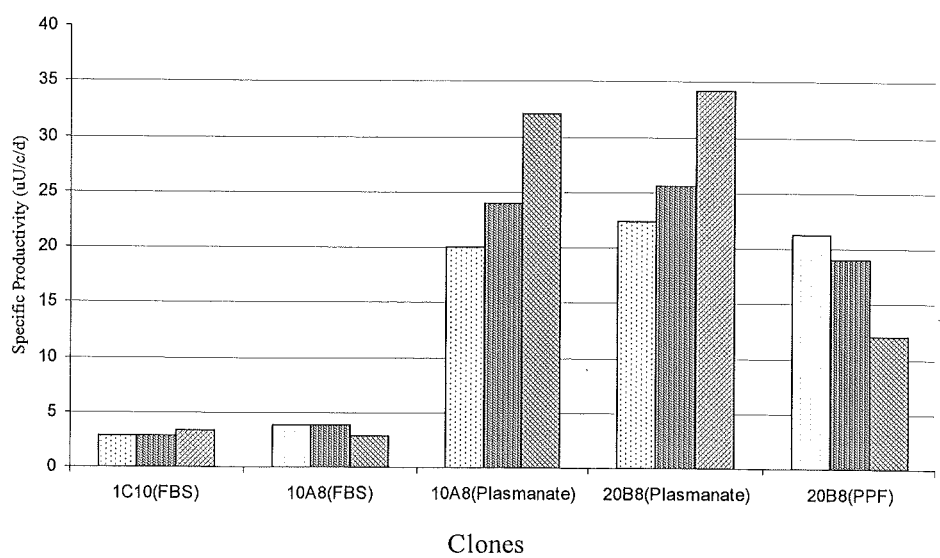

As summarized in FIG. 4(a), the initial population 1C10 was derived from the HKB cells transfected with pCIS25DTR after amplification with 400 nM MTX in the selection medium with 5% FBS. One of the first single cell clones (SCCs). 10A8, derived from 1C10 by a LDC using a selection medium supplemented with 5% FBS was adapted in serum-free medium supplemented with PLASMANATE® HPP fraction. Unexpectedly, 10A8 showed extremely increased levels of rFVIII production at this stage (FIG. 4b). Therefore, we did a second LDC using the medium supplemented with PLASMANATE® HPP fraction. The productivity of SCCs (e.g. 20B8) derived from the second LDC was similar with PLASMANATE® HPP fraction-adapted 10A8. 20B8 showed higher levels of BDD-FVIII than original 10A8 derived from the first LDC in serum-containing, medium. Finally, 20B8 was adapted to growth in plasma protein-free (PPF) medium. Samples of 20B8 were deposited at the American Type Culture Collection (Manassas, Va.) (ATCC deposit no. CRL-12582).

As shown in Table 1, HKB clones exhibit superior productivity for BDD-FVIII. A 10-20 fold increase in productivity was observed in HKB cells when compared to clones derived from transfected CHO and 293S cells. HKB cells, which do not form large aggregates of cells when grown in suspension culture, are preferred cells for the expression of proteins having factor VIII procoagulant activity.

TABLE 1

Expression of FVIII and BDD FVIII SQ in human and rodent cell lines

| FVIII Derivatives | Specific Productivity (µU/c/d)* | | | |
|---|---|---|---|---|
| | BHK | 293s | CHO | HKB |
| Full length FVIII | 0.45 | 1.2 | 0.5 | 1.0 |
| BDD FVIII SQ | ND | 2.5 | 1.0 | 20 |

*Average of 5 high producing clones (in serum-free media)
ND = Not done 1.6 Plasma-Protein-Free Adaptation of Clones HKB clones that have been adapted to grow as serum-free suspension cultures were further weaned of plasma protein supplements. The weaning was done in sterile polycarbonate shake flasks (Corning, Corning, N.Y.) at a cell density of about $0.5 \times 10^6$ cells/ml using plasma derived protein free medium. The plasma protein free (PPF) medium was DME/F12 medium supplemented with pluronic F68 (0.1%), $CuSO_4$ (50 nM), and $FeSO_4$/EDTA (50 μM). Complete medium exchange was done every 48 hours and the shake flasks were re-seeded at $0.5 \times 10^6$ cells/ml.

1.7 Fermentation of Clone 20B8

Figure 5:
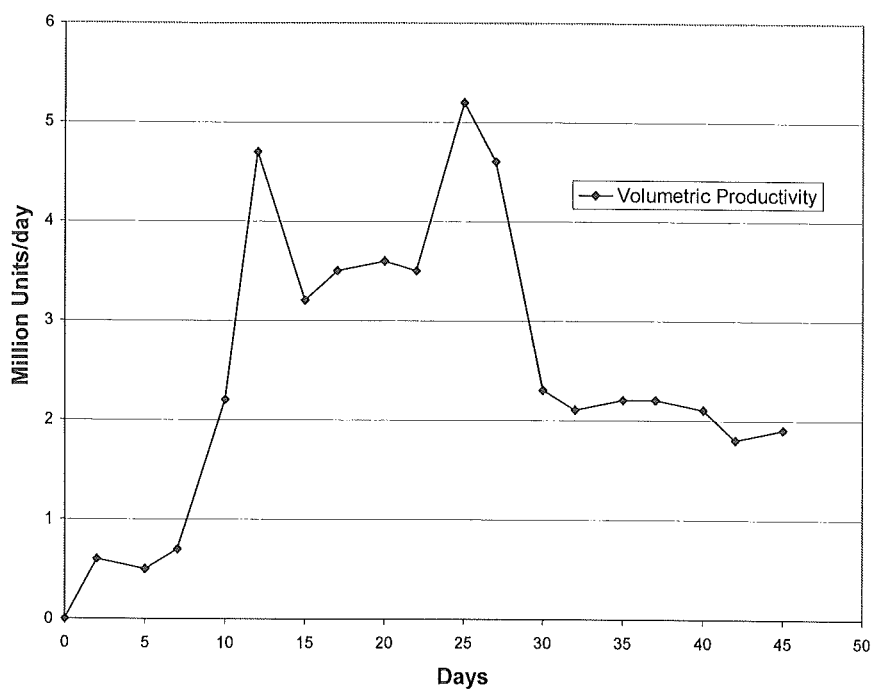
FIG. 5. Volumetric productivity of clone 20B8.

The productivity of clone 20B8 was evaluated in a 15-liter perfusion fermenter. The fermenter was seeded with clone 20B8 cells at a density of about $3 \times 10^6$ cells/ml. The fermenter was perfused at a rate of 4 volumes per day with the serum-free production medium as described in the preceding paragraph. A final cell density of $2 \times 10^7$ cells/ml was sustained throughout the evaluation period (45 days). As shown in FIG. 5, during the first 4 weeks of fermentation, clone 20B8 was perfused with the serumfree production medium supplemented with PLASMANATE® HPP fraction and was able to sustain high productivity. From day 28 to the end of the fermentation run, the cells were perfused with the same serumfree production medium but without PLASMANATE® HPP fraction. As shown in FIG. 5, the cells continued to produce high levels of FVIII in a plasma derived protein-free environment, "Plasma derived protein-free" means that essentially no proteins isolated from plasma have been added to the medium.

Example 2

Characterization of Type of Linkage of Sialic Acid of BDD FVIII SQ

BDD Factor VIII SQ was purified as described in Biochemistry 25:8343-8347 (1986) using ion exchange and affinity chromatography. The matrix 2,5-dihydroxybenzoic acid (DHB) was purchased from Aldrich Chemical Company, USA. HPLC grade trifluoroacetic acid (TFA) was from Pierce, USA. Baker analyzed HPLC grade acetonitrile was from J T Baker, USA. Newcastle disease virus neuraminidase was purchased from Sigma Chemical Co., USA. All consumable reagents for the GlycoPrep 1000, 2-amino benzamide (2-AB), GlycoSep C column, *A. ureafaciens* neuraminidase and standard oligosaccharides were purchased from Oxford GlycoSciences (OGS), Abingdon, UK.

Oligosaccharide analyses were done b dialyzing purified BDD FVIII SQ against MILLI-Q® purified water to remove salt and buffers. The desalted BDD FVIII SQ was dried in glass reactor vials for 18 hours using a SPEEDVAC® vacuum concentrator. Oligosaccharides were released by chemical hydrazinolysis using a GlycoPrep 1000 system from OGS. The liberated pool of oligosaccharides was filtered and dried immediately in a SPEEDVAC® vacuum concentrator to minimize the loss of terminal sialic acids.

The released total oligosaccharide pool was coupled to 2-aminobenzamide (2-AB). Briefly, oligosaccharides were dissolved in 5 ml of a solution of 2-AB (0.35M) in dimethylsulfoxide/glacial acetic acid (30% v/v) containing sodium cyanoborohydride (1 M). The glycan solution was then incubated at 65° C. for 2 h. After the conjugation with 2-AB, the reaction mixture was applied to a cellulose disk (1 cm in diameter) in a glass holder. The disk was washed with 1 ml of acetonitrile followed by 5×1 ml 4% deionized water in acetonitrile to remove unreacted dye and non-glycan materials. Labeled glycans were eluted using three washes (0.5 ml) of water and then filtered (0.2 mm).

Labeled oligosaccharides were separated with a DEAE anion-exchange column on the basis of their terminal sialic acid content. The column size was 4.6 mm×100 mm with a bed volume of 1.7 ml. A solvent gradient system of 0-200 mM ammonium acetate in 20% acetonitrile for 40 min at 0.3 ml/min was used. A high performance liquid chromatographic system equipped with an HP Ti-series 1050 pump (Hewlett Packard) was used to deliver the solvents and a programmable fluorescence detector (Hewlett Packard, model 1046A, $\lambda_{exc}$=330 nm and $\lambda_{emiss}$=420 nm) was used to detect 2-amino benzamide labeled oligosaccharide peaks.

Oligosaccharide pools were desialylated by digesting with either *Arthrobacter ureafaciens* (Sigma, cat no N-3642) or Newcastle disease virus (OGS, cat no. X-5017) neuraminidase in 50 mM sodium acetate buffer, pH 5.0 for 6 h or 18 h at 37° C. Digested samples were purified on a microcolumn containing 150 μL each of DOWEX® AG50, CHELEX® 100, DOWEX® AG3 and QAE SEPHADEX® ion exchange materials. Samples were eluted with water, then rotary-evaporated to dryness before analysis.

Figure 6:
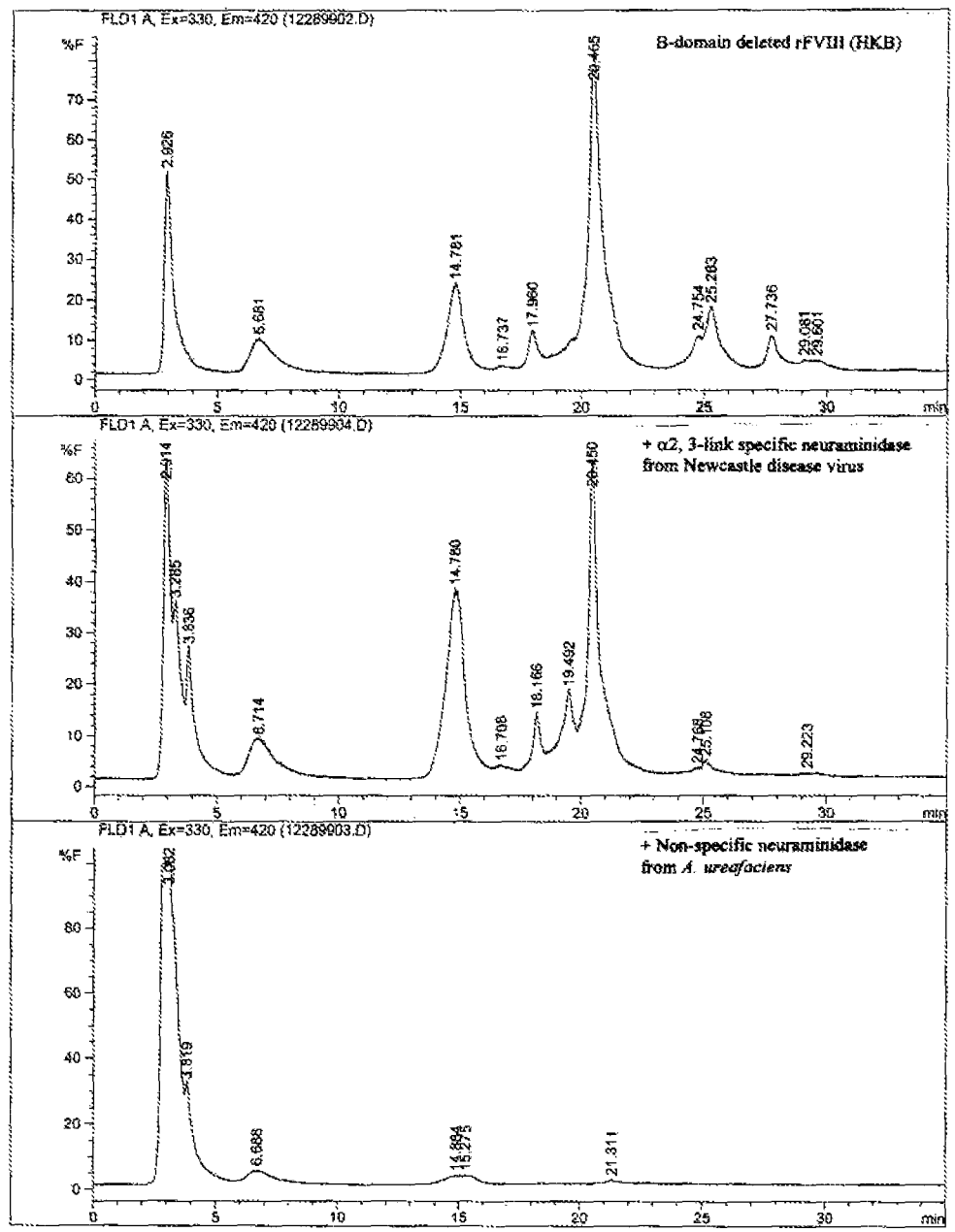
FIG. 6. Anion exchange chromatographic profile of 2-aminobenzamide labeled oligosaccharides from BDD FVIII SQ produced in HKB11 cells.

FIG. 6 shows the anion-exchange chromatographic profile of 2-aminobenzamide labeled oligosaccharides from BDD FVIII SQ As shown in the middle panel of FIG. 6, digestion of BDD FVIII SQ with neuraminidase from Newcastle disease virus that is specific for alpha (2,3)-linked sialic acid did not eliminate all the sialic acid peaks. Upon digestion of BDD FVIII SQ with neuraminidase from *A. ureafaciens* (capable of removing sialic acid of alpha (2,3) and alpha-(2,6) linkages), all the sialic acid peaks were eliminated (bottom panel of FIG. 6) as compared to undigested BDD FVIII SQ (top panel of FIG. 6). The neuraminidase digestion studies indicate that BDD FVIII SQ is capped with sialic acid of both alpha-(2,3) and alpha-(2,6) linkage.

Example 3

Characterization of Bisecting Oligosaccharide Linkage of BDD FVIII SQ Using MALDI Mass Spectrometric Analysis The 2,5-dihydroxybenzoic acid (DHB) matrix was prepared by dissolving 10 mg DHB in 1 mL 70% acetonitrile. Sample plates were dried after loading sample and matrix.

The mass spectrometer used to acquire the spectra was a VOYAGER DE-RP™ (PerSeptive Biosystems, Inc., Framingham, Mass.). All samples (protein and carbohydrates) were analyzed using delayed extraction mode and without the reflectron by irradiating with UV light (337 nm) from a $N_2$ laser. Neutral oligosaccharides were analyzed in the positive-ion mode at 25 kV using the DHB matrix. The delay time was set at 100 ns for oligosaccharide samples and at 150 ns for protein samples. The grid voltage was set to 94% and 89.5% of the accelerating voltage for oligosaccharides.

A two point external calibration (oligosaccharides high-mannose Man-5 [$(M+Na)^-_{Avg}$ 1258] and NA3 [desialylated triantennary, $(M+Na)^-_{Avg}$ 2029]) was used for mass assignment of the ions. Typically, spectra from 128-264 laser shots were summed to obtain the final spectrum.

As shown in FIG. 7 and Table 2, the FVIII-SQ has complex carbohydrate structures. These structures consist of biantennary, tri- and tetra-antennary oligosaccharide alditols. In addition, a unique bisecting GlcNAc was identified. This bisecting GlcNAc structure has been reported to be catalyzed by N-aceylglucosaminyltransferase, an enzyme known to be expressed in human cells.

TABLE 2

Major sodium ion (Na+)-associated oligosaccharide structures in HKB11-produced BDD FVIII SQ.

| Oligosaccharide Structures detected in HKB-rFVIII | Theoretical mass (with Na+ ion) | Observed mass (with Na+ ion) |
|---|---|---|
| $M_3Gn_2G_2$ (Biantennary) | 1664 | 1667 |
| $M_3Gn_2G_1Gn_b$ (Bisecting) | 1705 | 1708 |
| $M_3Gn_2G_2F$ (Biantennary + Fucosyl) | 1810 | 1812 |
| $M_3Gn_3G_3$ (Triantennary) | 2031 | 2033 |
| n.d. | ? | 2179 |
| $M_3Gn_4G_4$ (Tetraantennary) | 2392 | 2391 | n.d. Not-identified
Gn = N-acetylglucosamine; G = galactose; F = fucosyl; M = mannose The above examples are intended to illustrate the invention and it is thought variations will occur to those skilled in the art. Accordingly, it is intended that the scope of the invention should be limited only by the claims below.

The invention claimed is:

1. A method of producing an isolated glycosylated protein having factor VIII procoagulant activity comprising the amino acid sequence of SEQ ID NO: 1, the method comprising:
   obtaining cells comprising a heterologous nucleic acid encoding the protein;
   culturing the cells under plasma derived protein-free conditions to produce the protein, and
   isolating the protein thereby produced,
wherein the protein comprises an N-linked oligosaccharide having an alpha-(2,6)-linked sialic acid.

2. The method of claim 1, wherein the cells are obtained from human embryonic kidney cells.

3. The method of claim 1, wherein the cells are obtained from human embryonic kidney 293 cells.

4. The method of claim 1, further comprising the step of formulating the protein into a pharmaceutical preparation.

5. A method of producing an isolated glycosylated protein having factor VIII procoagulant activity comprising the amino acid sequence of SEQ ID NO: 1, the method comprising:
   obtaining cells comprising a heterologous nucleic acid encoding the protein;
   culturing the cells under plasma derived protein-free conditions to produce the protein, and
   isolating the protein thereby produced,
wherein the protein comprises an N-linked oligosaccharide comprising a bisecting GlcNAc linked to a core beta-mannose.

6. The method of claim 5, wherein the cells are obtained from human embryonic kidney cells.

7. The method of claim 5, wherein the cells are obtained from human embryonic kidney 293 cells.

8. The method of claim 5, further comprising the step of formulating the protein into a pharmaceutical preparation.

9. A method of producing an isolated glycosylated protein having factor VIII procoagulant activity comprising the amino acid sequence of SEQ ID NO: 1, the method comprising:
   culturing cells comprising a heterologous nucleic acid encoding the protein in plasma derived protein-free medium to express the protein, and
   isolating the protein thereby produced,
wherein the protein is expressed at a level of about 2 µU/c/d or greater.

10. The method of claim 9, further comprising the step of formulating the protein into a pharmaceutical preparation.

11. The method of claim 9, wherein the protein is expressed at a level of about 4 µU/c/d or greater.

12. The method of claim 11, further comprising the step of formulating the protein into a pharmaceutical preparation.

13. The method of claim 9, wherein the protein is expressed at a level of about 5 µU/c/d or greater.

14. The method of claim 13, further comprising the step of formulating the protein into a pharmaceutical preparation.

15. The method of claim 9, wherein the protein is expressed at a level of about 15 µU/c/d or greater.

16. The method of claim 15, further comprising the step of formulating the protein into a pharmaceutical preparation.

17. The method of claim 9, wherein the protein comprises an N-linked oligosaccharide having an alpha-(2,6)-linked sialic acid.

18. The method of claim 10, wherein the protein comprises an N-linked oligosaccharide having an alpha-(2,6)-linked sialic acid.

19. The method of claim 11, wherein the protein comprises an N-linked oligosaccharide having an alpha-(2,6)-linked sialic acid.

20. The method of claim 12, wherein the protein comprises an N-linked oligosaccharide having an alpha-(2,6)-linked sialic acid.

21. The method of claim 13, wherein the protein comprises an N-linked oligosaccharide having an alpha-(2,6)-linked sialic acid.

22. The method of claim 14, wherein the protein comprises an N-linked oligosaccharide having an alpha-(2,6)-linked sialic acid.

23. The method of claim 15, wherein the protein comprises an N-linked oligosaccharide having an alpha-(2,6)-linked sialic acid.

24. The method of claim 16, wherein the protein comprises an N-linked oligosaccharide having an alpha-(2,6)-linked sialic acid.

25. The method of claim 9, wherein the protein comprises an N-linked oligosaccharide comprising a bisecting GlcNAc linked to a core beta-mannose.

26. The method of claim 10, wherein the protein comprises an N-linked oligosaccharide comprising a bisecting GlcNAc linked to a core beta-mannose.

27. The method of claim 11, wherein the protein comprises an N-linked oligosaccharide comprising a bisecting GlcNAc linked to a core beta-mannose.

28. The method of claim 12, wherein the protein comprises an N-linked oligosaccharide comprising a bisecting GlcNAc linked to a core beta-mannose.

29. The method of claim 13, wherein the protein comprises an N-linked oligosaccharide comprising a bisecting GlcNAc linked to a core beta-mannose.

30. The method of claim 15, wherein the protein comprises an N-linked oligosaccharide comprising a bisecting GlcNAc linked to a core beta-mannose.

31. The method of claim 9, wherein the cells are obtained from human embryonic kidney cells.

32. The method of claim 9, wherein the cells are obtained from human embryonic kidney 293 cells.

33. A method of producing an isolated glycosylated protein having factor VIII procoagulant activity comprising the amino acid sequence of SEQ ID NO: 1, the method comprising:
   culturing cells comprising a heterologous nucleic acid encoding the protein in serum free medium supplemented with human plasma proteins to express the protein, and
   isolating the protein thereby produced,
wherein the protein is expressed at a level of about 10 µU/c/d or greater.

34. The method of claim 33, wherein the protein is expressed at a level of about 15 µU/c/d or greater.

35. The method of claim 33, wherein the protein is expressed at a level of about 20 µU/c/d or greater.

36. The method of claim 33, wherein the protein comprises an N-linked oligosaccharide having an alpha-(2,6)-linked sialic acid.

37. The method of claim 33, wherein the protein comprises an N-linked oligosaccharide comprising a bisecting GlcNAc linked to a core beta-mannose.

38. The method of claim 33, further comprising the step of formulating the protein into a pharmaceutical preparation.

* * * * *